United States Patent [19]

Wüst et al.

[11] Patent Number: 4,751,301

[45] Date of Patent: Jun. 14, 1988

[54] PROCESS FOR PREPARING BENZOTHIAZOLESULPHENAMIDES

[75] Inventors: Alfredo Wüst, Roesrath, Fed. Rep. of Germany; Tony van Osselaer, Belsele, Belgium

[73] Assignee: Bayer Aktiengesellschaft, Leverkusen-Bayerwerk, Fed. Rep. of Germany

[21] Appl. No.: 856,226

[22] Filed: Apr. 28, 1986

[30] Foreign Application Priority Data

May 11, 1985 [DE] Fed. Rep. of Germany ....... 3517084

[51] Int. Cl.$^4$ .................. C07D 277/80; C07D 413/12
[52] U.S. Cl. .................................... 544/135; 544/368; 546/198; 548/167; 548/168
[58] Field of Search ................ 544/135, 368; 546/198; 548/167, 168

[56] References Cited

U.S. PATENT DOCUMENTS 4,252,942  2/1981  Alicot et al. ...................... 548/168

FOREIGN PATENT DOCUMENTS 3430435  2/1986  Fed. Rep. of Germany.
413296   3/1933  United Kingdom.

OTHER PUBLICATIONS

Chemical Abstracts, vol. 92, No. 9, Mar. 3, 1980, p. 667, No. 76380u, Columbus, Ohio, U.S.; V. A. Ignatov et al., "Study of the Reaction by Bis(2-Benzothiazolyl)Disulfide with Amines".

Primary Examiner—Robert W. Ramsuer
Attorney, Agent, or Firm—Connolly & Hutz

[57] ABSTRACT

Benzothiazolesulphenamides can be prepared in high yield and purity from dibenzothiazolyl disulphide and a primary or secondary amine in the absence of an oxidizing agent in a water-immiscible organic solvent and in the presence of aqueous alkali by presenting a solution of the amine in the organic solvent and adding dibenzothiazolyl disulphide and aqueous alkali either simultaneously or in succession.

4 Claims, No Drawings

PROCESS FOR PREPARING BENZOTHIAZOLESULPHENAMIDES

The invention relates to a process for preparing benzothiazolesulphenamides from dibenzothiazolyl disulphides and water-soluble amines.

Benzothiazolesulphenamides are customarily prepared by oxidative coupling of 2-mercaptobenzothiazoles, their alkali metal salts or disulphides and primary or secondary amines (German Offenlegungsschriften (published specifications) 2,356,686 and 2,744,423). In this process, either the yields obtained in relation to and based on mercaptobenzothiazole are only moderate and the products are contaminated by by-products which impair the storage life of the sulphenamide, or it is necessary to use involved and uneconomical processes featuring complicated purification steps.

In relation to the amines, the known processes produce yields of at most 90%. This is a significant disadvantage, since the sulphenamides, which as is known are used as vulcanization accelerators, are made, inter alia, from amines which are at least as costly to prepare as the mercaptobenzothiazole portion.

It is further known from Izv. vyssh. Uchebn. Zaved., Khimiya i khim. tekhnol., 22 (1979), 9, 1067–1070 to react dibenzothiazolyl disulphide (MBTS) with amines in the presence and absence of alkali and in the absence of an oxidation agent.

Without alkali and using morpholine as the amine a yield of 86% was obtained in relation to the conversion, which admittedly was only 50%, since the formation of one mole of sulphenamide is accompanied by the formation of one mole of the morpholine salt of mercaptobenzothiazole, which needs to be additionally worked up in a separate operation using sodium hydroxide solution.

If sodium hydroxide solution is added in order to produce a sodium salt of mercaptobenzothiazole (NaMBT) as a reusable by-product and to reduce the amount of amine to be used, the yield of sulphenamide drops as a function of the sodium hydroxide solution down to 10%.

It is the object of the invention to provide an economical process for preparing purer benzothiazole sulphenamides having improved storage lives in improved yield.

It has now been found, surprisingly, that the reaction of MBTS with primary or secondary amines in the absence of oxidizing agents in a water-immiscible organic solvent in which the resulting sulphenamide is soluble and in the presence of aqueous alkali it is possible in high yield to give pure benzothiazolyl sulphenamides if certain conditions are complied with in controlling the reaction.

The invention therefore provides a process for preparing benzothiazolesulphenamides from dibenzothiazole disulphide and a primary or secondary amine in the absence of an oxidizing agent in a water-immiscible organic solvent and in the presence of aqueous alkali, characterized in that a solution of the amine is presented in the organic solvent and dibenzothiazolyl disulphide and aqueous alkali are added either simultaneously or in succession. It is also possible to suspend the dibenzothiazolyl disulphide in the organic solvent and then to add the amine, followed by the aqueous alkali.

The aqueous alkali is added in such a way as to set a pH value of 10 to 13, preferably 11 to 12. The reaction is carried out at a temperature 0° to 80° C., preferably 20° to 60° C.

The two liquid phases are separated. By evaporating the organic phase the sulphenamide is obtained and the solvent and the amine are recovered.

The aqueous phase is made to yield excess amine (by distillation) and mercaptobenzothiazole (by precipitation with acid).

The aqueous alkali can be in particular sodium hydroxide solution and potassium hydroxide solution.

Suitable solvents are for example toluene and xylene.

Suitable amines are in particular n-propylamine, isopropylamine, n-butylamine, tert.-butylamine, pentylamines, cyclopentylamine, cyclohexylamine, dimethylamine, diethylamine, morpholine, piperazine, pyrolidine and piperidine.

The process according to the invention is particularly useful if cyclohexylamine, isopropylamine, tert.-butylamine and morpholine are used.

The process can be carried out not only discontinuously but also continuously.

EXAMPLE 1

4-(2-Benzothiazolylthio)-morpholine

In a two-liter multineck flask equipped with a stirrer, dropping funnel, condenser, thermometer and pH electrode, 435 g of morpholine and 1000 g of toluene were placed. At 20°–30° C. 332 g of dibenzothiazolyl disulphide were added in small portions in the course of 20–30 minutes. At the same time, 200 g of 20% strength sodium hydroxide solution were added dropwise, so that the pH was between 10 and 13. After the addition had ended, stirring was continued for one hour, the two phases were separated, and the aqueous phase was extracted with 500 g of toluene. The combined organic phases gave after evaporation 4-(2-benzothiazolylthio)-morpholine in 99.5% strength yield. The product had an active substance content of 99%, a free amine content of 0.1%, a methanol-insolubles content of 0% and a melting point of 85.5°–87° C. for a heating-up rate of 1° C./min. These values remained unchanged after 24 hours of ageing in a water-moist atmosphere.

EXAMPLE 2

60 g of cyclohexylamine were dissolved in 455 g of toluene. 100 g of dibenzothiazolyl disulphide and 12.1 g of NaOH, dissolved in 170 g of water, were added in succession. After 10 minutes the toluene phase was separated from the aqueous phase, was washed with water and was evaporated at 65° C. in vacuo.

This gave 79.5 g of N-cyclohexylbenzothiazolesulphenamide (100% of theory) having a purity of 97%. The free amine content was 1%.

The aqueous phase was acidified, and the precipitated MBT was filtered off and dried. This gave 45.9 g (91.2% of theory) having a purity of 97.4%.

We claim:

1. Process for preparing benzothiazolesulphenamides from dibenzothiazolyl disulphide and a primary or secondary amine in the absence of an oxidizing agent in a water-immiscible organic solvent and in the presence of aqueous alkali, characterized in that a solution of the amine in the organic solvent is presented and dibenzothiazolyl disulphide and aqueous alkali are added either simultaneously or in succession, with the aqueous alkali being added at such a rate as to set a pH of 10 to 13 and with the reaction being carried out at 0° to 80° C.;

2. Process according to claim 1, characterized in that the aqueous alkali is added at such a rate as to set a pH of 11 to 12.

3. Process according to claim 1, characterized in that the reaction is carried out at 20° to 60° C.

4. Process according to claim 1, characterized in that the amine used is cyclohexylamine, isopropylamine, tert.-butylamine or morpholine.

* * * * *